US012727756B2

(12) United States Patent
Kieturakis

(10) Patent No.: US 12,727,756 B2
(45) **Date of Patent: *Sep. 8, 2026**

(54) METHODS AND SYSTEMS FOR ROBOTIC SINGLE-PORT LAPAROSCOPIC ACCESS

(71) Applicant: Maciej J. Kieturakis, Los Altos Hills, CA (US)

(72) Inventor: Maciej J. Kieturakis, Los Altos Hills, CA (US)

(73) Assignee: Maciej J. Kieturakis, Los Altos Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/819,618

(22) Filed: Aug. 29, 2024

(65) Prior Publication Data

US 2025/0235093 A1 Jul. 24, 2025

Related U.S. Application Data

(63) Continuation of application No. 18/338,988, filed on Jun. 21, 2023, now Pat. No. 12,102,302, which is a (Continued)

(51) Int. Cl.
*A61B 34/30* (2016.01)
*A61B 1/313* (2006.01)
*A61B 34/20* (2016.01)

(52) U.S. Cl.
CPC ............ *A61B 1/3132* (2013.01); *A61B 34/20* (2016.02); *A61B 34/30* (2016.02);
(Continued)

(58) Field of Classification Search
CPC ....... A61B 1/3132; A61B 17/29; A61B 34/30; A61B 34/20; A61B 34/71; A61B 17/3423;
(Continued)

(56) References Cited

U.S. PATENT DOCUMENTS 6,171,282 B1 1/2001 Ragsdale
6,454,783 B1 9/2002 Piskun
(Continued)

FOREIGN PATENT DOCUMENTS

WO WO-2019246202 A1 12/2019
WO WO-2021046657 A1 3/2021
WO WO-2023212089 A1 11/2023

OTHER PUBLICATIONS

Kim et al., A Novel Surgical Manipulator with Workspace-Conversion Ability for Telesurgery, 2012, IEEE, pg., 200-211 (Year: 2012).*

(Continued)

*Primary Examiner* — McDieunel Marc
(74) *Attorney, Agent, or Firm* — Wilson Sonsini Goodrich & Rosati

(57) ABSTRACT

A laparoscopic tool has a semicircular mid-portion with a center point and coinciding remote center of the robotic arm, to which the tool is mounted on a common axis located between straight proximal and straight distal sections. The straight proximal of the laparoscopic tool is rotatably mounted on a fixed side mount on surgical robotic arm. The robotic arm is disengaged from the surgical robot to allow manual location of the robotic arm to position the semicircular mid-portion through a percutaneous port and the center point of semi-circular mid-portion and coinciding remote center of the robotic arm, to which the tool is mounted at a target virtual insertion point on the patient's body. Visual aids are provided to assist in the positioning of the center point.

21 Claims, 12 Drawing Sheets

Related U.S. Application Data continuation of application No. 18/172,290, filed on Feb. 21, 2023, now Pat. No. 11,717,149.

(60) Provisional application No. 63/335,548, filed on Apr. 27, 2022.

(52) U.S. Cl.
CPC . *A61B 2034/2059* (2016.02); *A61B 2034/302* (2016.02); *A61B 2034/305* (2016.02)

(58) Field of Classification Search
CPC ........... A61B 34/37; A61B 2017/2901; A61B 2034/2059; A61B 2090/3937; A61B 2017/2906; A61B 2034/301; A61B 2034/305; A61B 2017/00738; A61B 2034/302; A61B 2090/309
See application file for complete search history.

(56) References Cited

U.S. PATENT DOCUMENTS

| | | | | |
|---|---|---|---|---|
| 6,459,926 | B1 | 10/2002 | Nowlin et al. | |
| 6,587,750 | B2 | 7/2003 | Gerbi et al. | |
| 6,594,552 | B1 | 7/2003 | Nowlin et al. | |
| 6,879,880 | B2 | 4/2005 | Nowlin et al. | |
| 7,087,049 | B2 | 8/2006 | Nowlin et al. | |
| 7,373,219 | B2 | 5/2008 | Nowlin et al. | |
| 7,386,365 | B2 | 6/2008 | Nixon | |
| 7,778,733 | B2 | 8/2010 | Nowlin et al. | |
| 7,806,891 | B2 | 10/2010 | Nowlin et al. | |
| 8,506,555 | B2 | 8/2013 | Ruiz Morales | |
| 9,295,379 | B2 * | 3/2016 | Sholev | A61B 34/25 |
| 9,317,651 | B2 | 4/2016 | Nixon | |
| 10,512,481 | B2 | 12/2019 | Cooper | |
| 11,291,510 | B2 | 4/2022 | Shelton, IV et al. | |
| 11,311,342 | B2 | 4/2022 | Parihar et al. | |
| 11,324,536 | B2 | 5/2022 | Kieturakis | |
| 11,369,443 | B2 | 6/2022 | Shelton, IV et al. | |
| 11,424,027 | B2 | 8/2022 | Shelton, IV | |
| 11,504,192 | B2 | 11/2022 | Shelton, IV et al. | |
| 11,564,756 | B2 | 1/2023 | Shelton, IV et al. | |
| 11,596,486 | B2 | 3/2023 | Rabindran et al. | |
| 11,717,149 | B1 | 8/2023 | Kieturakis | |
| 2003/0045778 | A1 | 3/2003 | Ohline et al. | |
| 2004/0176751 | A1 | 9/2004 | Weitzner et al. | |
| 2006/0167440 | A1 | 7/2006 | Cooper et al. | |
| 2006/0241414 | A1 | 10/2006 | Nowlin et al. | |
| 2007/0021738 | A1 | 1/2007 | Hasser et al. | |
| 2007/0049966 | A1 | 3/2007 | Bonadio et al. | |
| 2009/0093752 | A1 | 4/2009 | Richard et al. | |
| 2009/0163931 | A1 | 6/2009 | Cooper et al. | |
| 2011/0071541 | A1 | 3/2011 | Prisco et al. | |
| 2011/0118709 | A1 | 5/2011 | Burbank | |
| 2011/0124970 | A1 | 5/2011 | Kleyman | |
| 2011/0251464 | A1 | 10/2011 | Kleyman | |
| 2011/0295074 | A1 | 12/2011 | Stefanchik et al. | |
| 2012/0095297 | A1 | 4/2012 | Dang et al. | |
| 2012/0116362 | A1 | 5/2012 | Kieturakis | |
| 2012/0157781 | A1 | 6/2012 | Kleyman | |
| 2012/0190933 | A1 | 7/2012 | Kleyman | |
| 2012/0245428 | A1 | 9/2012 | Smith et al. | |
| 2013/0116712 | A1 | 5/2013 | Belson | |
| 2013/0253279 | A1 | 9/2013 | Smith | |
| 2014/0188130 | A1 | 7/2014 | Sanchez et al. | |
| 2016/0081752 | A1 | 3/2016 | Kieturakis | |
| 2016/0184030 | A1 | 6/2016 | Seeber et al. | |
| 2016/0235496 | A1 | 8/2016 | Hoffman et al. | |
| 2019/0307474 | A1 | 10/2019 | Kieturakis | |
| 2020/0367982 | A1 | 11/2020 | Abbott | |
| 2020/0405143 | A1 * | 12/2020 | Fowler | A61B 1/126 |
| 2020/0405403 | A1 | 12/2020 | Shelton, IV et al. | |
| 2021/0038313 | A1 * | 2/2021 | Sholev | A61B 34/30 |
| 2022/0096120 | A1 | 3/2022 | Bajo et al. | |
| 2023/0121709 | A1 | 4/2023 | Xu et al. | |
| 2024/0180413 | A1 | 6/2024 | Kieturakis | |

OTHER PUBLICATIONS

Hagn et al., Telemanipulator for remote minimally invasive surgery, 2008, IEEE, p. 1-11 (Year: 2008).*
Zahraee et al., Toward the Development of a Hand-Held Surgical Robot for Laparoscopy, 2010, IEEE, pg., 853-861 (Year: 2010).*
Zhang et al., Cooperative robotic assistant for laparoscopic surgery: CoBRASurge, 2009, IEEE, pg., 5540-5545 (Year: 2009).*
Abbott et al. Design of an Endoluminal NOTES Robotic System. Proceedings of the 2007 IEEE/RSJ International Conference on Intelligent Robots and Systems, San Diego, CA Oct. 29-Nov. 1, 2007 pp. 410-416.
Anderson et al. Comparing a Mechanical Analogue With the Da Vinci User Interface: Suturing at Challenging Angles. IEEE Robotics and Automation Letters 1(2):1060-1065 (Jul. 2016).
Can, et al. Design, Development and Evaluation of a Highly Versatile Robot Platform for Minimally Invasive Single-port Surgery. The Forth IEEE RAS/EMBS International Conference on Biomedical Robotics and Biomechatronics Roma, Italy Jun. 24-27, 2012 pp. 817-822.
Chin et al. Single Port Robotic Surgery—Does this advance our field? UCLA. pp. 1-23 (Mar. 2021).
Gungor et al. Single-Port Robotic Practice. Textbook of Gynecologic Robotic Surgery. pp. 27-33 (2018).
Kaouk et al. Single-Port Laparoscopic and Robotic Partial Nephrectomy. European Urology 55:1163-1170 (2009).
Noonan et al. An Articulated Universal Joint Based Flexible Access Robot for Minimally Invasive Surgery. 2011 IEEE International Conf. on Robotics and Automation; Shanghai China, May 9-13, 2011 pp. 1-6.
PCT/US2019/037903 International Search Report and Written Opinion dated Sep. 10, 2019.
PCT/US2023/020034 International Search Report and Written Opinion dated May 31, 2023.
Piccigallo et al. Design of a Novel Bimanual Robotic System for Single-Port Laparoscopy. IEEE/ASME Transactions on Mechatronics 15(6):871-878 (Dec. 2010).
Riojas, et al. A Hand-Held Non-Robotic Surgical Tool With a Wrist and an Elbow. IEEE Transactions on Biomedical Engineering 66(11):3176-3184 (2019).
Shang, et al. Design of a Multitasking Robotic Platform With Flexible Arms and Articulated Head for Minimally Invasive Surgery. IEEE/RSJ International Conference on Intelligent Robots and Systems Oct. 7-12, 2017 pp. 1988-1993.
U.S. Appl. No. 16/444,275 Notice of Allowance dated Jan. 24, 2022.
U.S. Appl. No. 16/444,275 Office Action dated Sep. 10, 2021.
U.S. Appl. No. 18/172,290 Notice of Allowance dated May 19, 2023.
U.S. Appl. No. 18/338,988 Notice of Allowance dated Jul. 31, 2024.
U.S. Appl. No. 18/338,988 Office Action dated Jun. 14, 2024.
Xie et al. Current Status of Single Port Laparoscopic/Robotic Surgeries for Urogenital Cancers. 2021, IEEE, pp. 1-4.
EP23797222.9 Extended European Search Report dated Mar. 6, 2026.

* cited by examiner

METHODS AND SYSTEMS FOR ROBOTIC SINGLE-PORT LAPAROSCOPIC ACCESS

CROSS-REFERENCE TO RELATED APPLICATIONS

This application is a continuation of U.S. patent application Ser. No. 18/338,988, filed Jun. 21, 2023, which is a continuation of U.S. patent application Ser. No. 18/172,290, filed Feb. 21, 2023, now U.S. Pat. No. 11,717,149, issued Aug. 8, 2023, which claims the benefit of U.S. Provisional No. 63/335,548, filed Apr. 27, 2022, the entire content of which is incorporated herein by reference.

BACKGROUND OF THE INVENTION

1. Field of the Invention

The present invention relates generally to medical systems, tools, and methods. More particularly, the present invention relates to systems and tools for robotically assisted laparoscopic access, typically for access of multiple robotically manipulated tools through a single incision in the umbilicus or other location.

In recent years, many open surgical procedures performed in the abdominal cavity have been replaced by minimally invasive procedures performed through several very small incisions using an endoscope, referred to as a laparoscope, inserted through one of the incisions. The other incisions are used for introducing surgical tools, and the abdominal cavity is inflated to create a space for performing the surgery. Such procedures are commonly called "laparoscopic", and can be used for gallbladder removal, hernia repair, hysterectomy, appendectomy, gastric fundoplication, and other procedures. Similar endoscopic, thoracoscopic and other procedures are performed in other body cavities with or without inflation.

While a great advance over open surgical procedures, which can require an incision of several inches or more through the abdominal wall, such laparoscopic procedures still require incisions through muscle or fascia in several separate sites. Each incision may increase the risk of infection, bleeding trocar site hernia, increased postoperative pain, compromised cosmetic result and other adverse events for the patient.

As an improvement over such laparoscopic procedures, "single port" laparoscopy has been proposed where a single access port is inserted through the umbilicus (the patient's navel). Access solely through the umbilicus is advantageous since it provides superior cosmetic and functional results. Introducing the laparoscope and all other tools necessary for the surgery through a single port, however, makes performance of the procedures more difficult. In particular, the use of conventional laparoscopic tools, which are typically straight, makes it difficult to approach a single target area in the treated tissue with two or more tools at the same time.

Further improvements in the field of single port laparoscopic surgery are described in U.S. Patent Publications 2012/0116362, 2016/0081752, and 2019/0307474, commonly assigned with the present application, the full disclosures of which are incorporated herein by reference. As generally described in these applications, systems for performing single port laparoscopic procedures include a transcutaneous seal and a plurality of tools. The tools comprise a substantially rigid tubular sleeve having a C-shaped central region and an effector core which is translatably and rotatably disposed in the sleeve. The C-shaped central region of the tubular sleeve, typically formed as a semicircle, physically passes through the single port while a "center point" of the semicircle and is aligned with a "virtual" insertion site on the patient's abdominal wall for that tool. Such a virtual insertion site acts as a fulcrum point for the tool as it is manipulated even though the tool physically passes through a single port location offset from the virtual insertion site. Two, three, or even more such tools may have C-shaped central regions physically passing through the single port with their virtual remote centers positioned radially outwardly from a center defined by the single port.

Of particular interest to the present invention, US2019/0307474 describes a method for rigidly attaching such laparoscopic tools, i.e., those having C-shaped central regions to robotic arms. Such rigid attachment, however, limits the ability of a physician to manually position the surgical arm and align the tool prior to commencing a robotic surgical procedure. Unlike conventional straight laparoscopic tools, laparoscopic tools having C-shaped central regions require that the center points of the C-shaped central regions be aligned with "virtual" remote centers of the robotic surgical systems, i.e., the sites where straight laparoscopic tools would have been inserted for manipulation by the robotic surgical systems.

Thus, it would be beneficial to provide improved methods, systems, and apparatus for the robotic manipulation of laparoscopic tools having C-shaped central regions, such as those described in U.S. Patent Publications 2012/0116362, 2016/0081752, and 2019/0307474, commonly assigned with the present application. It would be particularly desirable if the improved methods, systems and apparatus, allowed a physician to manually position a C-shaped central region of a laparoscopic tool carried by a robot arm through a single port, manually align the C-shaped segment center point located in the remote center of the attached robotic arm with the virtual point of insertion, while the C-shape segment passes through the actual insertion point and freely move the center point to alternative virtual insertion sites without the need to remove the laparoscopic tool from the single port or penetrate the patient's skin at any target virtual insertion site. Such improved methods, systems and apparatus will preferably facilitate multiple tool access to abdominal and other surgical target sites through the single port at the patient's umbilicus or elsewhere with minimum interference between adjacent tools during the performance of a procedure. At least some of these objectives will be met by the inventions described hereinafter.

2. Description of the Background Art

U.S. Patent Publications 2019/0307474; 2012/0116362; and 2016/0081752 have been described above. Surgical robotic systems of the type suitable for use with the laparoscopic tools of the present invention are described in US2009/0163931; US2014/0188130; US2011/0118709; US2013/0116712; US2016/0235496; US2007/0021738; and US2003/0045778. Other patent publications of interest include US2011/0071541; US2007/0049966; US2006/0167440.

SUMMARY OF THE INVENTION

In a first aspect of the present invention, a laparoscopic tool is configured to be mounted on a surgical robotic arm which includes a fixed side mount (configured for detachably coupling to a straight laparoscopic or other cannula) and a driver interface. The laparoscopic tool comprises a shaft having (a) a straight proximal section, (b) a straight distal section axially aligned along a common axis with the straight proximal section, (c) a semicircular mid-portion having a center point on the common axis and located between and contiguous with the straight proximal and straight distal sections, and (d) a central passage extending therethrough. A flexible cable assembly is configured to pass through the central passage of the shaft and to accommodate the semicircular mid-portion as the flexible cable wire assembly is axially translated and rotated in the central passage of the shaft. A driven interface on the straight proximal section of the shaft is configured to be detachably connected to the driver interface on the robot arm to manipulate the flexible cable assembly, and a distal effector extends from the straight distal section of the shaft and is drivably coupled to a distal end of the flexible cable assembly. A rotatable side mount rotatably is coupled to the straight proximal section of the shaft, and the side mount is configured to detachably connect to the fixed side mount on the robot arm and to allow the common axis of the shaft to be rotated about at least two axes orthogonal to a longitudinal axis of the surgical robotic arm.

In some instances, the side mount is coupled to the straight proximal section of the shaft by a pair of orthogonally oriented rotational joints.

In some instances, the laparoscopic tool further comprises a telescoping section extending distally of the distal effector end of the shaft to accommodate extension and retraction of the flexible cable wire assembly. Typically, but not necessarily, the segments of the telescoping section have alignment features that prevent relative rotation as the segments are extended and retracted.

In some instances, the flexible cable assembly is configured to be rotatably and translatably attached to the driver interface in the surgical robot arm so that said driver interface can axially and rotationally reposition a push/pull wire of the flexible cable wire assembly relative to the common axis of the shaft to actuate the distal effector. In such instances, the flexible cable assembly may further comprise a bidirectional torque tube located coaxially over the push/pull and being configured to transmit torque and axial translation forces from the driver interface in the robot arm to the distal effector.

In a second aspect of the present invention, a laparoscopic tool system for use with a surgical robot comprises a laparoscopic tool and an alignment tool. The laparoscopic tool may be configured in any of the ways described and claimed herein, and the alignment tool is typically coupled to the shaft of the laparoscopic tool and configured to visually "mark" the position of the center point of the semicircular mid-portion of the shaft and the remote center of the robotic arm, to which the tool is mounted to facilitate manual positioning of the surgical robot arm with mounted tool to place the center point at a target virtual point of insertion. The remote center corresponds to a "virtual" tool insertion site, i.e., a site at which an abdominal wall or other cavity wall penetration would have been made to accommodate a straight laparoscopic tool.

In conventional robotic surgery using straight laparoscopic cannulas and tools, the "remote center" (also referred to as the "remote center of motion") is the point in space where the cannula and inserted tool pass through the abdominal wall and enter the patient's body. This point of entry serves as a fixed fulcrum which limits lateral repositioning of the cannula after insertion. Moreover, each robotic arm and tool has a separate remote center and abdominal penetration. As described in detail bellow, the tools of the present invention allow remote centers, i.e., virtual insertion points, to be moved without requiring additional penetrations and often without even removing the tool from the patient.

In some instances, the alignment tool is detachably coupled to the shaft.

In some instances, the alignment tool is an elongated body having a proximal end coupled to the shaft and a distal marking tip positioned at the center point when the proximal end is coupled to the shaft.

In other instances, the alignment tool is configured to project a pair of visible beams which cross at the center point of the semicircular mid-portion of the tool when the alignment tool is coupled to the shaft. In this way, the center point of the semicircular mid-portion of the tool aligned with the remote center of the robotic arm, to which the tool is mounted, can be positioned precisely at the virtual point of insertion on the patient's abdominal wall by manually positioning the robotic arm so that the beams cross precisely at the desired location of the virtual insertion point on the patient's abdomen or other skin region.

In both cases, alignment of the center point of the semicircular mid-portion of the tool with the remote center of the robotic arm occurs at the time the tool is attached to the robotic arm. From this point on the center point of the semicircular mid-portion and the remote center of the robotic arm will remain coincident in space, i.e., at the same location in space even as the laparoscopic tool and the supporting robot arm is moved in space.

In a third aspect of the present invention, a method for performing robotic surgery with at least one laparoscopic tool having an axis and remote center aligned with a target virtual point of insertion on a patient's abdomen comprises providing (a) a surgical robotic system having at least one robotic arm which includes a fixed side mount and a driver interface and (b) at least one laparoscopic tool having a semicircular mid-portion with a center point on a common axis located between and contiguous with a straight proximal section and a straight distal section. The straight proximal section of the shaft is rotatably coupled to the fixed side mount on the robot arm such that the common axis of the shaft can be rotated about at least two axes orthogonal to a longitudinal axis of the surgical robotic arm. The semicircular mid-portion of the shaft of the at least one laparoscopic tool is positioned through a percutaneous passage, and the at least one robotic arm is disengaged from the surgical robot so that the at least one robotic arm can be manually positioned.

The at least one robotic arm is manually positioned to locate the center point of the semicircular mid-portion of the shaft (which is coincident with the remote center of the robot arm) of the at least one laparoscopic tool at the target "virtual" point of insertion for the tool on the body surface. That is, even though the tool physically passes through a different location, such as a "single port" located through the patient's umbilicus or other location, manipulations of the tool by the robot arm can be controlled as if the tool were straight and passing through the "virtual" point of insertion.

The laparoscopic tool of the present invention is typically attached to the robot arm while the semicircular mid-portion remains positioned through the single port or other percutaneous passage, causing the common axis of the at least one laparoscopic tool to self-rotate and align relative to the longitudinal axis of the surgical robotic arm. After the at least one robotic arm is engaged with the surgical robot, the robotic arm is manipulated to cause an end effector on at least one laparoscopic tool to surgically interact with tissue while the mid-portion of the shaft remains positioned in the percutaneous passage and the center point remains located at the remote center previously set on the patent's abdomen.

In some instances, manually positioning the at least one robotic arm to locate the center point of the semicircular mid-portion of the shaft and coinciding remote center of the robotic arm, to which the tool is mounted of the at least one laparoscopic tool with the virtual insertion point on the patent's abdomen comprises providing a visual marker of the location of the center point on the patient's abdomen and aligning the visual marker with the location of a target virtual point of insertion. For example, providing the visual marker of the location of the center point on the patient's abdomen may comprise coupling an elongated body having a distal marking tip positioned at the center point to the shaft. In another example, providing a visual marker of the location of the center point on the patient's abdomen may comprise projecting a pair of visible beams which cross at the center point on the patient's abdomen.

In some instances, rotatably coupling the straight proximal section of the shaft to the fixed side mount on the robot arm comprises detachably attaching a rotatable side mount rotatably coupled to the straight proximal section of the shaft to the fixed side mount on the robot arm. For example, the rotatable side mount may be rotatably coupled to rotate about at least two axes orthogonal to a longitudinal axis of the surgical robotic arm.

In some instances, the method as described above may further comprise providing a second laparoscopic tool having a semicircular mid-portion with a center point on a common axis located between and contiguous with a straight proximal section and a straight distal section. The straight proximal section of the shaft of the second laparoscopic tool is rotatably coupled to a fixed side mount on a second robot arm of the surgical robot such that the common axis of the shaft of the second laparoscopic tool can be rotated about at least two axes orthogonal to a longitudinal axis of the second surgical robotic arm. The semicircular mid-portion of the shaft of the second laparoscopic tool is positioned through the percutaneous passage, and the second robotic arm from the surgical robot is disengaged so that the second robotic arm can be manually positioned. The second robotic arm is manually positioned to locate the center point of the semicircular mid-portion of the shaft and coinciding remote center of the robotic arm, to which the tool is mounted of the second laparoscopic tool with a second virtual point of insertion on the patient's abdomen while the semicircular mid-portion remains positioned through the percutaneous passage, causing the common axis of the second laparoscopic tool to self-rotate and align relative to the longitudinal axis of the second surgical robotic arm. The second robotic arm is then re-engaged with the surgical robot so that the second robotic arm is again manipulated by the surgical robot. Once re-engaged, the surgical robot is operated to manipulate the second robotic arm to cause an end effector on the second laparoscopic tool to surgically interact with tissue while the mid-portion of the shaft of the second laparoscopic tool remains positioned in the percutaneous passage and the center point and remote center of the second robotic arm remains located at the second virtual point of insertion on the patent's abdomen.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
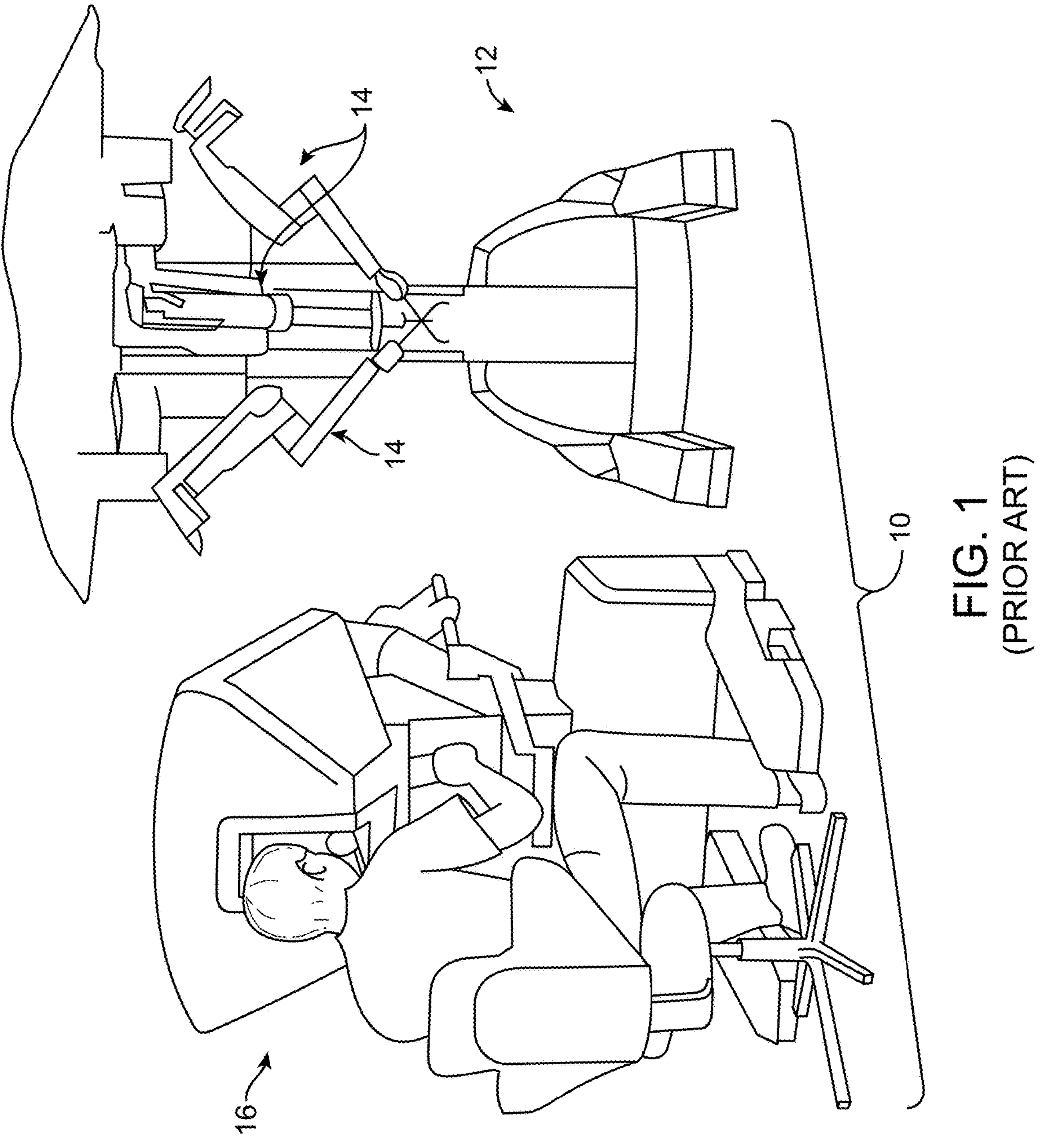
FIG. 1 illustrates a commercially available robotic surgical system of the type that can be used to manipulate the laparoscopic tools of the present invention.

Referring now to FIG. 1, the laparoscopic tools and end effectors of the present invention are intended to be used with and manipulated by known and commercially available robotic systems, such as a da Vinci® Surgical System available from Intuitive Surgical, Inc., Sunnyvale, California. An exemplary robotic surgery system 10 includes a robotic station 12 that includes a plurality of robotic arms 14 (with three being illustrated) and a controller module 16 where a physician can view the procedure and control the surgical arms to manipulate the tools to perform a desired laparoscopic or other surgery.

Figure 2:
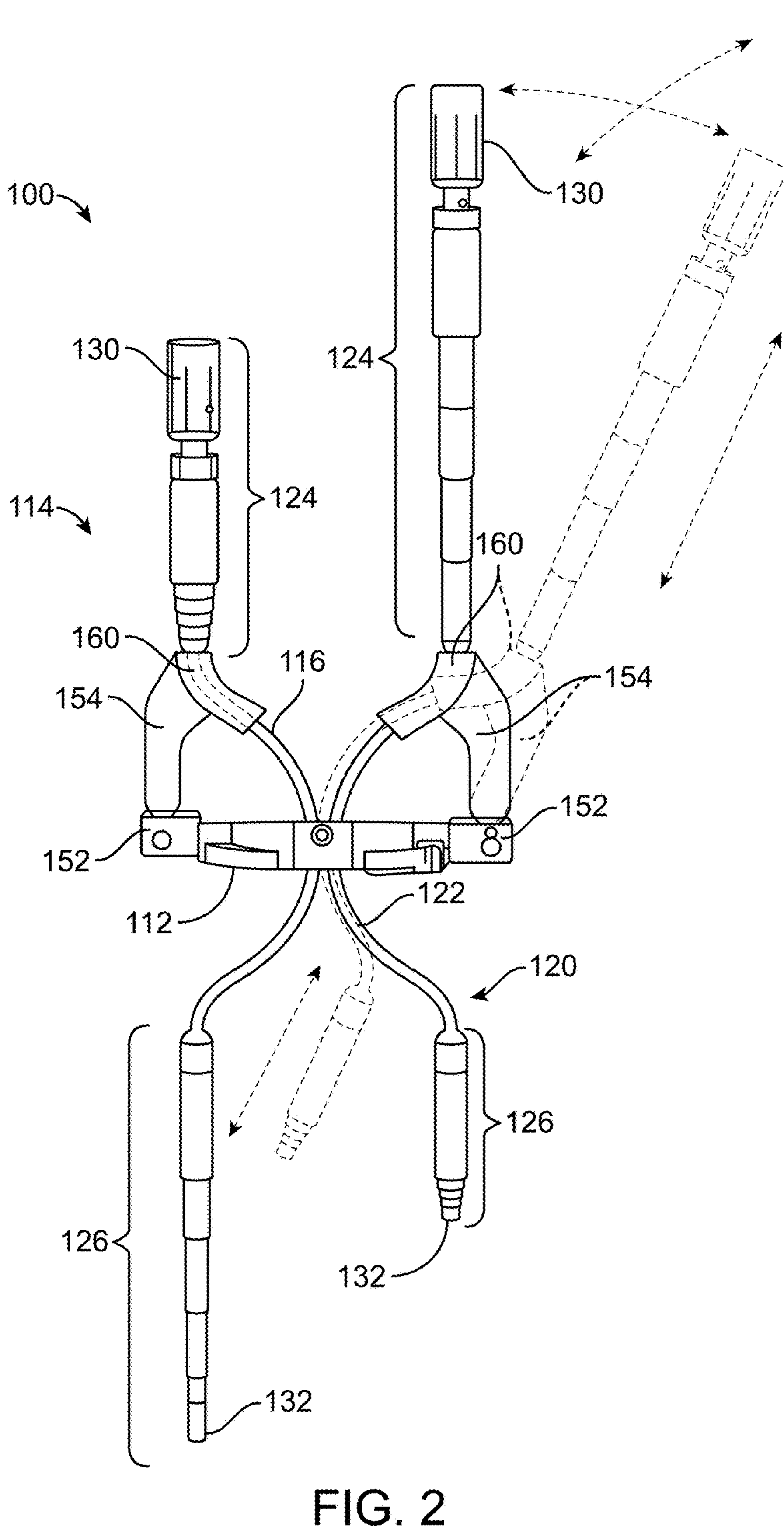
FIG. 2 illustrates a pair of laparoscopic tools intended for manual manipulation in surgical procedures where said tools are intended for single port access and are pivotally mounted in a support frame, with a repositioned view of one of the tools shown in broken line.
Figure 3:
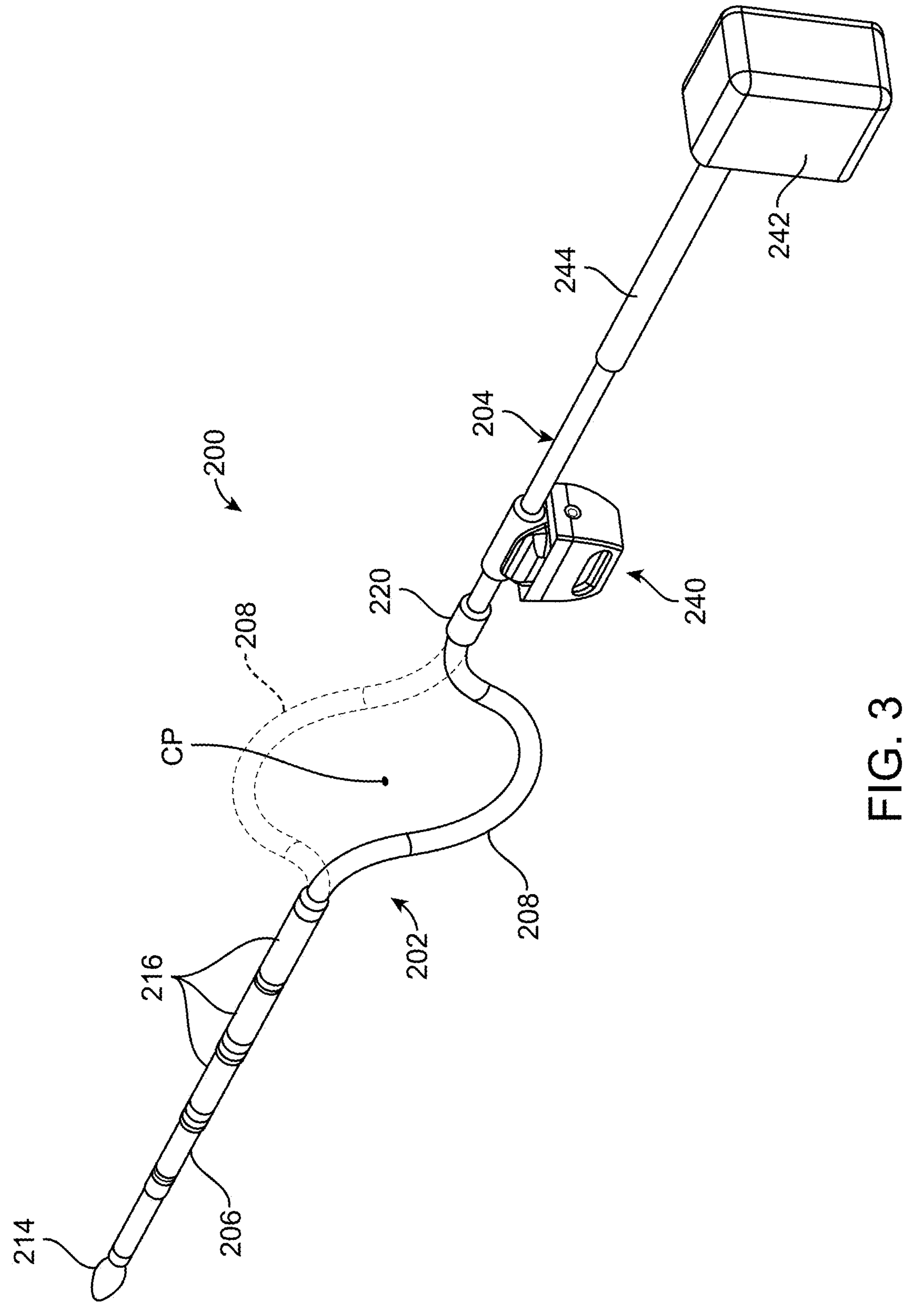
FIG. 3 is a perspective view of a laparoscopic tool constructed in accordance with the principles of the present invention and configured for manipulation by the arm of a surgical robot.

Referring now to FIGS. 2, a prior art laparoscopic tool system 100 of the type described in US2016/0081752, previously incorporated herein by reference, comprises a tool attachment frame 112 having a first tool 114 and a second tool 120 pivotally attached thereto. The first tool has a mid-portion 116 and the second tool has a mid-portion 122, and both mid-portions extend generally inwardly from an axis 128 of the tool. Both mid-portions 116 and 122 are preferably circular and have a radius emanating from a virtual rotation point which is generally aligned with a pivot 152 of an assembly attached to an outer periphery of the tool attachment frame 112. Having the virtual rotation points of each tool located outside the periphery of the ring in the location of double pivot allows the generally circular mid-portions 116 and 22 to pass and move through the central opening 118 of the frame 112 without interfering with each other. While the mid-portions 116 and 22 could alternatively have non-circular geometries which extend radially inward relative to the frame 112, for example being oval or polyhedral, the circular shape causes the passage point of the mid-portion to remain fixed within the central opening 118 of the frame so long as the tool is constrained to move in to orthogonal planes by the pivot attachment as will be explained in more detail hereinafter. While in some instances, it would be possible to modify the arms of a surgical robot to manipulate these prior art tools, these tools are intended to be manually manipulated and any attempt to directly interface the look with a robotic arm would be suboptimum.

Referring now to FIGS. 3 and 4A-4D, a laparoscopic tool 200 constructed in accordance with the principles of the present invention comprises a shaft 202 having a straight proximal section 204 and a straight distal section 206 separated by a semi-circular mid-portion 208. The straight proximal section 204 and the straight distal section 206 are aligned along a common longitudinal axis, and the straight proximal section has a rotational connector 220 positioned proximal to the semicircular mid-portion 208 which allows the semicircular mid-portion and straight distal section to rotate relative to the straight proximal section 204 about the common longitudinal axis. Such ability to rotate is essential to allow repositioning of the laparoscopic tool 200 to different virtual insertion points (which will act as remote center locations for the robotic system) without removal from the patient and while the tool remains attached to a robot arm as will be described in more detail below. Typically, the proximal section 204 includes a sleeve 244 which telescopically relieves another portion of the proximal section to allow length adjustment.

The laparoscopic tool 200 further includes an end effector 214, such as forceps, cutters electrosurgical elements, or the like, at its distal end, and the distal section 206 will typically have a telescopic construction to allow its length to be adjusted. A rotatable side mount 240 is attached to the proximal section 204 of the shaft 202 at a location proximal to the rotational connector, and the rotatable side mount is configured to be removably attached to a robotic arm of a surgical robot, as will be described in more detail below. In this way, all portions of the shaft 202 distal to the rotatable connector 220 will be free to rotate about the longitudinal axis of the shaft, and in particular, the semicircular mid-portion 208 will be able to rotate to other positions as shown, for example, in broken line in FIG. 3.

Figures 4A, 4B, 4C, 4D:
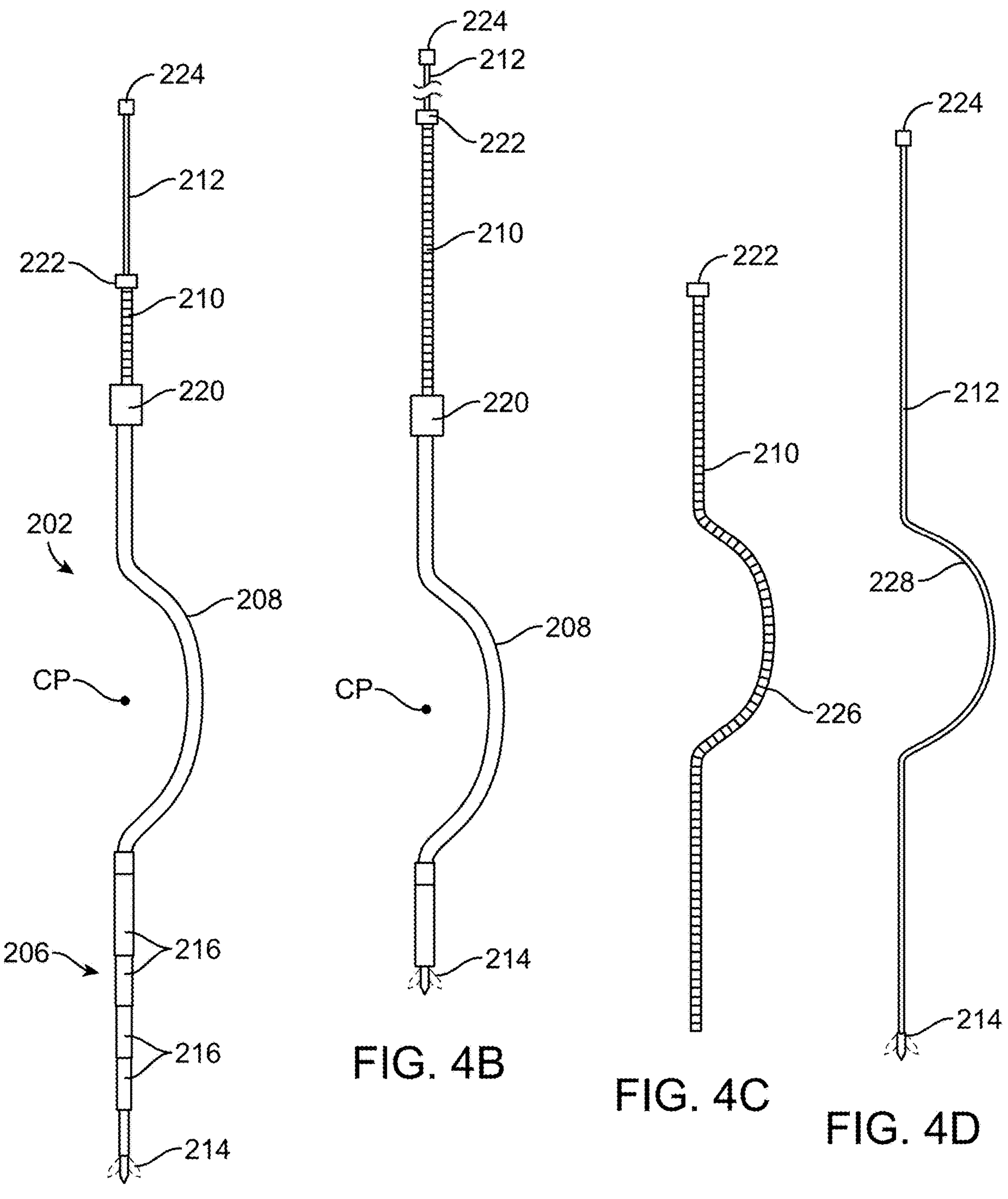
FIGS. 4A-4D illustrate internal components of the laparoscopic tool of FIG. 3 with FIGS. 4A and 4B showing an extended and a retracted telescopic distal extension, respectively, and FIGS. 4C and 4D showing a flexible cable and wire configured to actuate an end effector.

Referring now to specifically FIGS. 4A to 4B, the internal components of the laparoscopic tool 200 which allow manipulation of the end effector 214 will be described. The shaft 202 has a hollow central passage which receives a flexible cable 210. The flexible cable 210 has a hollow lumen extending from a distal end to a proximal end thereof which receives a pull and/or push wire 212 having an end effector 214 at its distal end. The flexible cable 210 has a proximal attachment member 222 at its proximal end, and the pull and/or push wire 212 has a proximal attachment member 224 at its proximal end. The distal section 206 of the shaft 202 is preferably joined as a telescoping structure having a plurality of segments 216 including a distal-most segment 218 that carries the end effector 214. The telescoping distal section may be axially extended and retracted to accommodate full axial extension of the flexible cable 210, as illustrated in FIG. 4A, as well as full axial retraction of the flexible cable, as illustrated in FIG. 4B. The flexible cable 210, by nature of its flexibility, provides a conformable central region 226 to accommodate bending as the cable passes through a preferred C-shaped mid-portion 208 of the shaft. Similarly, the pull/push wire 212 will have a conforming region 228 to accommodate bending as it is extended and retracted through the conforming region 226 of the flexible cable 210. The surgical robot manipulates the end effector 214 via these internal components using a drive head 286 mounted on a tool holder 282 which connects to the robotic arm interface 242 on the laparoscopic tool 200 when the tool is mounted on the tool holder of the surgical robot, as shown in FIG. 10 described below.

The robotic arm interface 242 allows the drive head 286 of robotic surgical system to mechanically drive the end effector 214 by manipulating the internal components of the laparoscopic tool 200. Axial translation of the cable and wire assembly (including the flexible cable 210 and pull/push wire 212) relative to the shaft 202 can be achieved by selectively tensioning the proximal attachment member 222 at the proximal end of the flexible cable 210. Similarly, rotation of the cable and wire assembly about the assembly's longitudinal axis can also be achieved by rotating the proximal attachment member 222 at the proximal end of the flexible cable 210. In addition, axial translation of the pull/push wire 212 relative to the flexible cable 210 to actuate an end effector may be achieved by manipulation of the proximal attachment 224 at the proximal end of the pull/push wire 212.

Figure 9:
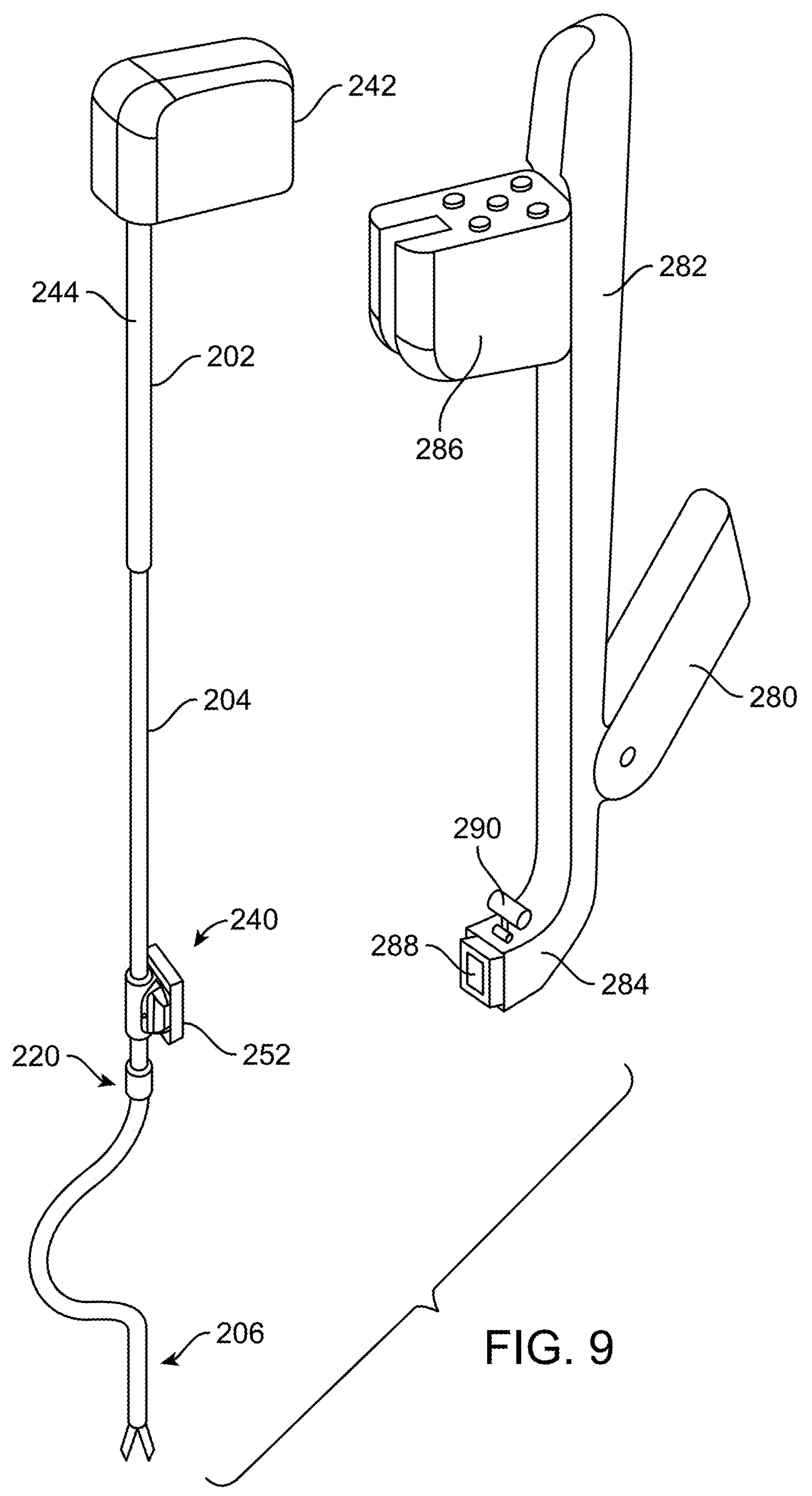
FIG. 9 illustrates a laparoscopic tool of the present invention adjacent to an arm of a surgical robotic system prior to mounting of the tool on the arm.
Figure 10:
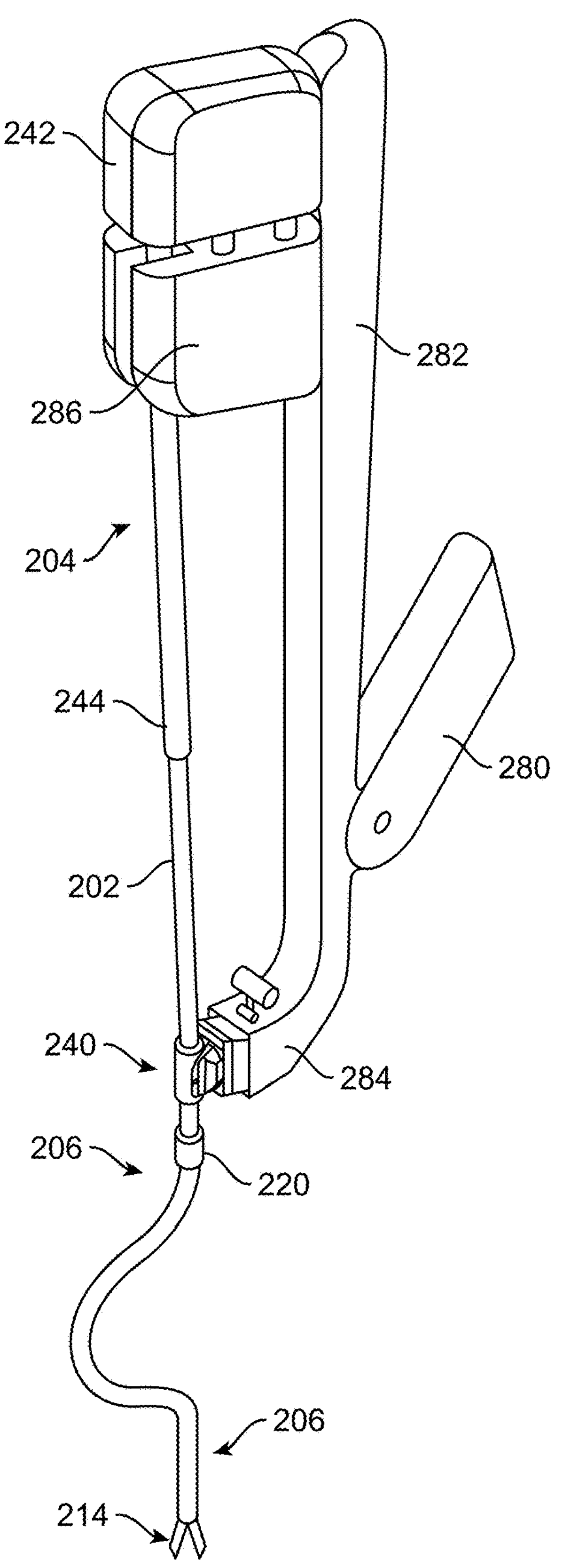
FIG. 10 illustrates the laparoscopic tool and surgical robot arm of FIG. 9 with the tool mounted on the arm.

The proximal section 204 of the laparoscopic tool 200 is secured to tool the holder 282 through attachment of the robotic arm interface 242 to the drive head 286, as seen in FIGS. 9 and 10, while the distal section 206 of the laparoscopic tool is secured to tool the holder through attachment of the rotatable side mount 240 to a tool attachment head 284 at a lower end of the tool holder, as also seen in FIGS. 9 and 10. The specific connection between the robotic arm interface 242 and the drive head 286 will depend on the nature of the laparoscopic tool and does not form part of the present invention. Usually, the specific connection pattern for the tools of the present invention will be arranged to match that of a corresponding conventional laparoscopic tool of the same type, e.g., all forceps all cutters will be interfaced similarly, and the robotic control system will be agnostic to the use of the conventional tools or the tools of the present invention. In contrast, the rotatable side mount 240 is designed to provide one or more rotational axes to facilitate connection of the laparoscopic tool 200 to the tool holder 282.

Figure 5:
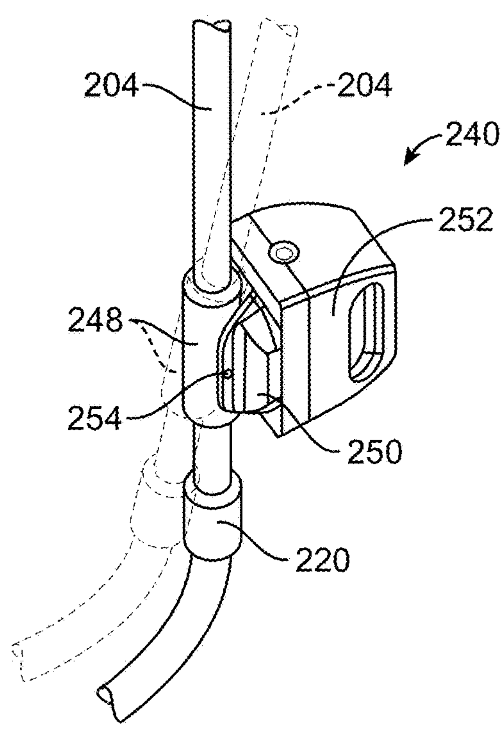
FIG. 5 is a detailed view of a side connector attached to a proximal section of a shaft of the laparoscopic tool of FIG. 3 showing rotation of the side connector about a first axis transverse to the shaft in broken line.
Figure 6:
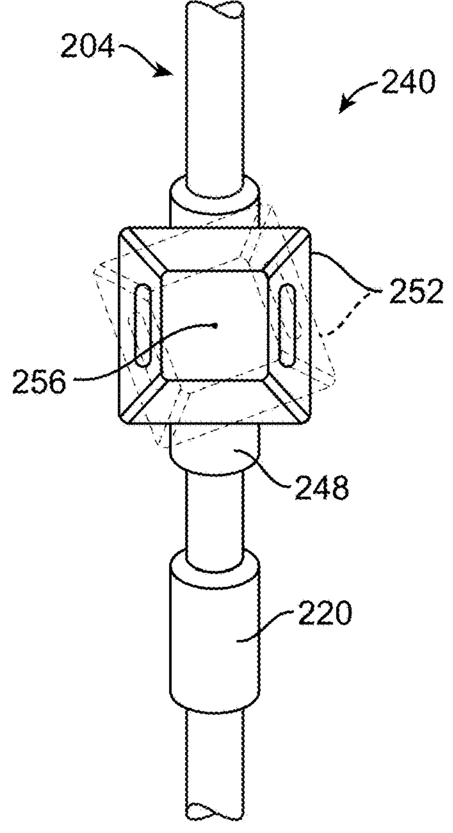
FIG. 6 is a detailed view of the side connector of the laparoscopic tool of FIG. 3 showing rotation of the side connector about a second axis transverse to the shaft in broken line.

Referring now to FIGS. 5 and 6, the rotatable side mount 240 comprises a base cylinder 248, a base plate 250, and an insertable connector 252. The base cylinder 248 is crimped or other fixed to the outer surface of the proximal section 204 of the shaft 202 on a proximal side of the rotatable connector 220. The base plate 250 is pivotally attached to the base cylinder 248 at a pivot axis 254 so that it can tilt relative to the shaft as shown in broken line in FIG. 5. The insertable connector 252 is pivotally attached to the base plate 250 at a pivot axis 256 so that it can rotate relative to the shaft as shown in broken line in FIG. 6. In this way, the insertable connector 252 has two orthogonal pivot axes relative to the axis of the shaft 202 which allows the laparoscopic tool to be first connected at its lower end to the tool holder 282 and then reoriented as the robotic arm interface 242 is connected the drive head 286 at the upper end of the tool holder.

Figures 7, 8:
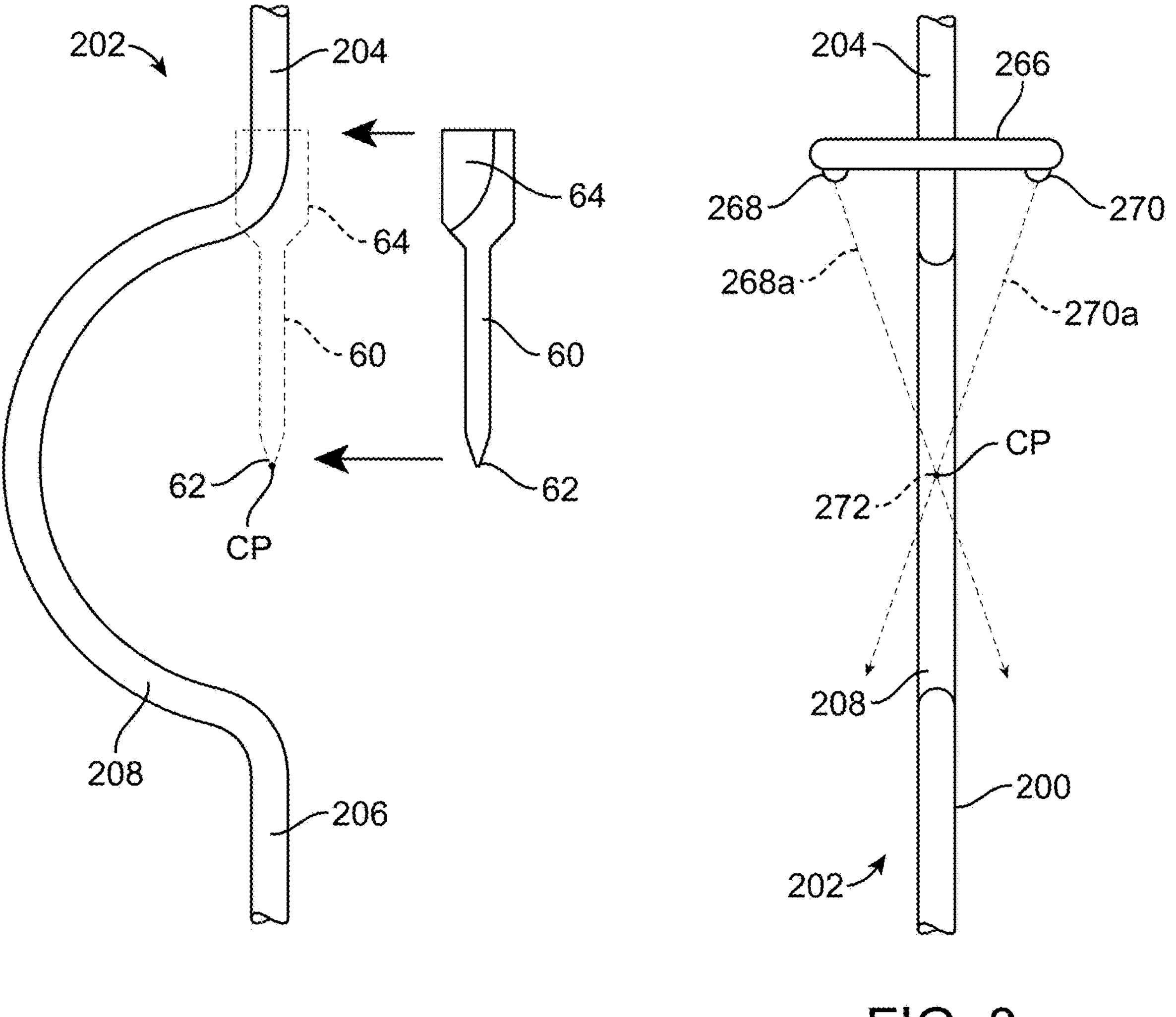
FIG. 7 illustrates a first embodiment of an alignment tool attachable to the shaft the laparoscopic tool of the present invention configured to allow a user to align a center point of the tool with a remote center utilized of the robotic system.
FIG. 8 illustrates a second embodiment of an alignment tool attachable to the shaft the laparoscopic tool of the present invention configured to allow a user to align a center point of the tool with a remote center utilized of the robotic system.

Referring now to FIGS. 7 and 8, an alignment tool is typically coupled to the shaft of the laparoscopic tool and configured to visually "mark" the position of the center point CP of the semicircular mid-portion of the shaft to facilitate manual positioning of the surgical robot arm to place the center point/remote center at a target "virtual point of insertion" on the patient's body. As shown in FIG. 7, an alignment tool 260 may be a simple straight rod or probe have a tip 262 with locates at the center point CP when a connector hub 264 is removably attached to the proximal section 204 of the shaft 202, as shown in broken line. As shown in FIG. 8, an alignment tool 266 comprises a bar with a pair of light emitting diodes or other light sources 268 and 270 which are arranged to project beams 268*a* and 268*b* that cross at point 272 which is located at the center point CP of the semi-circular mid-portion of the shaft 202. The laparoscopic tool 200 can thus be aligned by manually moving the laparoscopic tool 200 and tool holder 282 until the tip 62 of alignment tool 260 or the cross point 272 of alignment tool 266 is located at a target virtual point of insertion, as will be described in greater detail with reference to FIGS. 11A-11E below.

FIG. 9 illustrates the laparoscopic tool 200 of the present invention adjacent to a tool holder 282 carried by an arm 280 of a surgical robotic system, such as that illustrated in FIG. 1, prior to mounting of the tool on the arm. The laparoscopic tool 200 is mounted by inserting the insertable connector 252 of the rotatable side mount 240 into an attachment cavity 288 on one side of the attachment head 284 of the tool holder 282. Mount release lever 290 allows the tool 200 to be released from the tool holder 282 after a procure has been completed. Typically, the rotatable side mount 240 of the laparoscopic tool 200 will attached to the attachment head 284 of the tool holder 282 prior to attaching the robotic interface 242 to the drive head 286. In this way, the shaft 202 of the laparoscopic tool 200 remains free to rotate relative to the mounting axes defined by the rotatable side mount 240, as described previously with reference to FIGS. 5 and 6. Once the attachment head 284 is attached to the tool holder 282, as shown in FIG. 10, the laparoscopic tool 200 will be immobilized with respect to the tool holder 282, and the laparoscopic tool 200 and the tool holder 282 will be moved together as one unit by the surgical robot arm 280. The attachment head 284 of the tool holder 282 will typically include a clutch release (not shown) which allows the user to selectively disengage the surgical robot arm 282 so that it can be manually positioned relative to a patient for initial set up, as will be described in greater detail with reference to FIGS. 11A-11E.

Figures 10A, 10B:
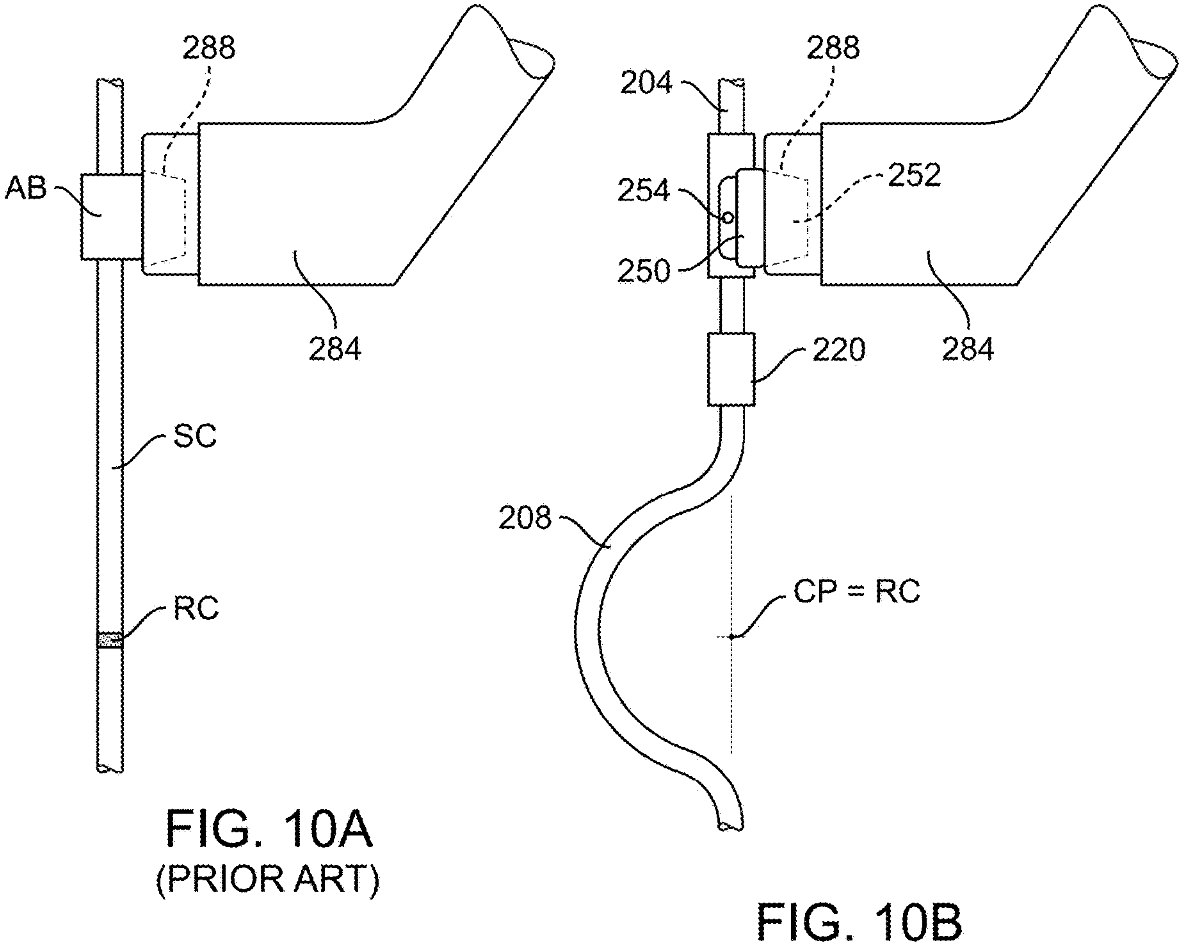
FIG. 10A illustrates connection of a prior art straight laparoscopic tool to a tool holder of a robotic surgical system showing the location of a "remote center" characteristic of the robotic surgical system marked on the straight laparoscopic tool.
FIG. 10B illustrates connection of the laparoscopic tool of the present invention to a tool holder of a robotic surgical system showing the location of a "remote center" characteristic of the robotic surgical system coincident with the center point of semicircular mid-portion of the laparoscopic tool in free space.

FIG. 10A illustrates connection of a straight laparoscopic tool, such as straight cannula SC, to the attachment head 284 of the tool holder of a robotic surgical system showing the location of a "remote center RC" characteristic of the robotic surgical system marked on the straight laparoscopic tool. The location of the remote center RC is marked on a shaft of the cannula SC so that a user may locate the remote center an actual abdominal wall penetration in a conventional robotic laparoscopic surgical procedure. The remote center is a characteristic of the particular surgical system being employed and is the fulcrum or pivot point of the tool shaft and is used by the robotic surgical system to plan all manipulation of the tool FIG. 10B illustrates connection of the laparoscopic tool of the present invention to the attachment head 284 of a tool holder of a robotic surgical system showing the location of a "remote center" characteristic of the robotic surgical system. In contrast to the conventional, straight tool illustrated in FIG. 10B, however, the remote center RC will be coincident with the center point CP of semicircular mid-portion of the laparoscopic tool which is located in free space. In further contrast to the conventional, straight tool illustrated in FIG. 10B, the remote center RC of the laparoscopic tools of the present invention will be positioned at a virtual insertion site without the need for an actual penetration. By dimensioning the laparoscopic tool of the present invention to locate the center point CP of the semicircular mid-portion at the remote center of the particular robotic surgical system to be used, the robotic surgical system will be able to manipulate the tool as if it were straight, so no modifications to the robotic surgical system are necessary (although there may be instances where modifications might be useful).

Figure 11A:
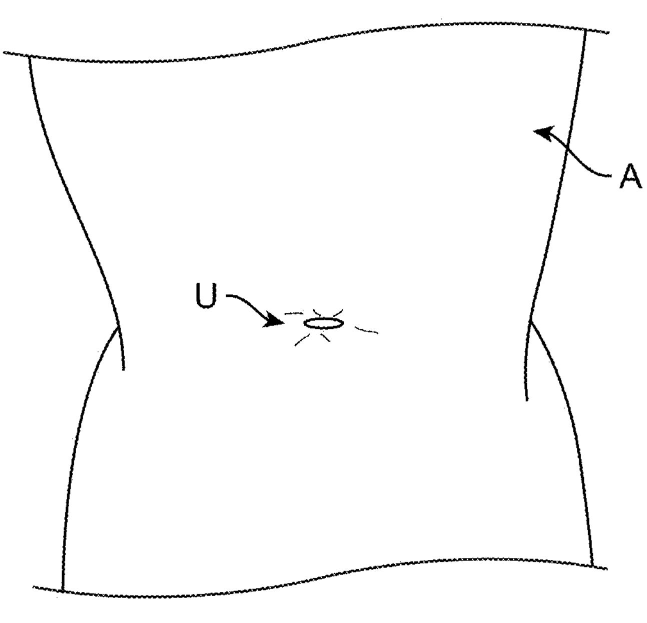
FIGS. 11A-11E illustrate a method for performing robotic surgery with a laparoscopic tool having an axis aligned with a target remote center on a patient's abdomen in accordance with the principles of the present invention.
Figure 11B:
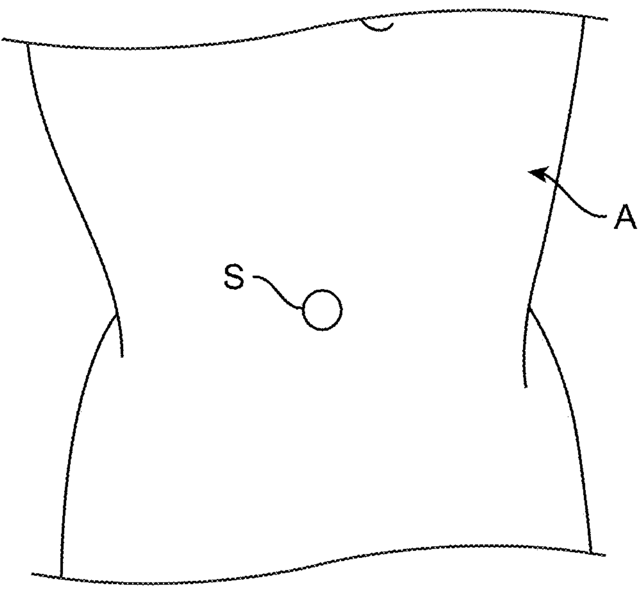
Figures 11C, 11D:
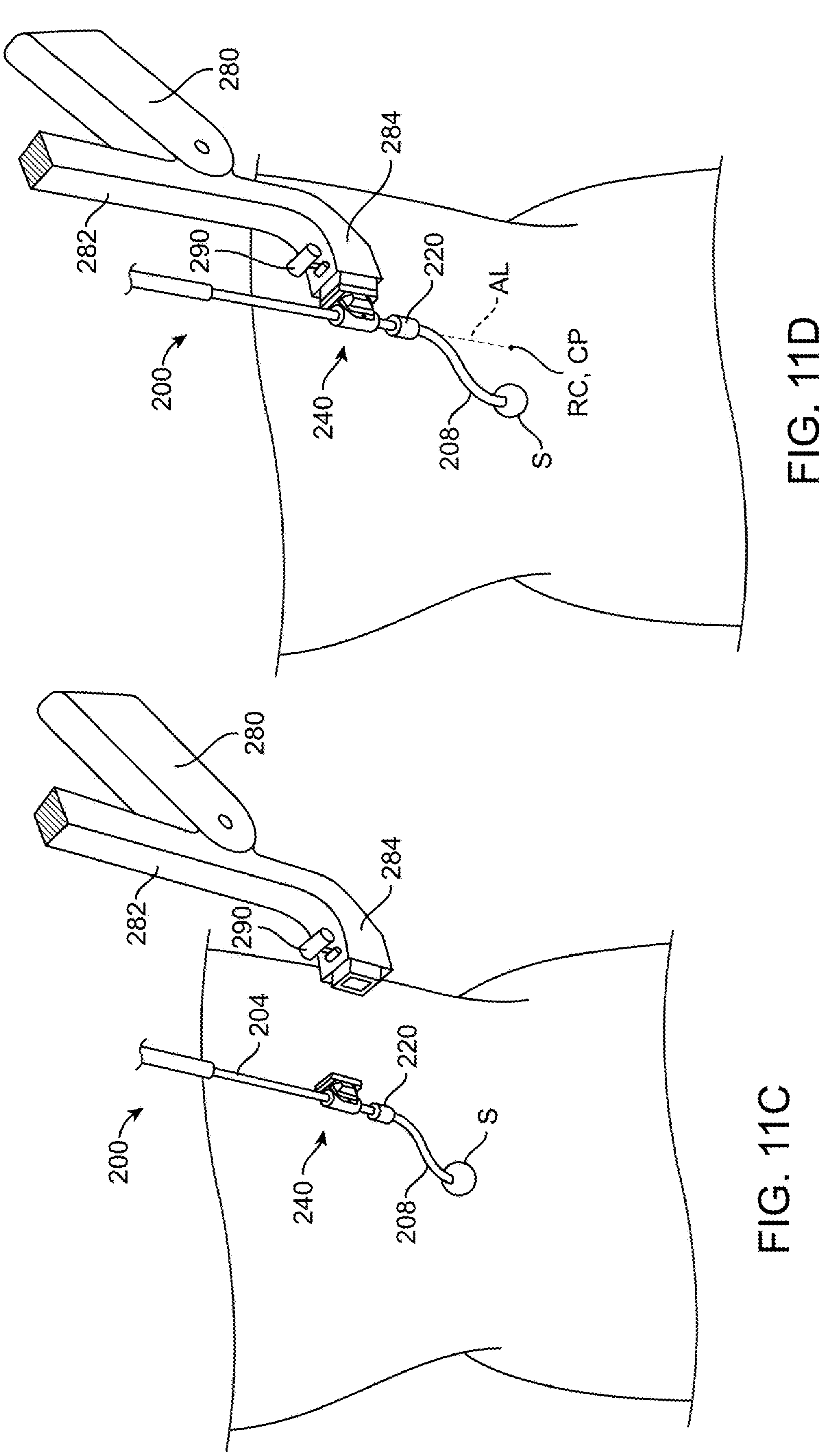

A method for positioning the laparoscopic tools of the present invention will now be described with reference to FIGS. 11A-11E. As shown in FIGS. 11A and 11B, a laparoscopic port or seal S, such as that described in commonly owned US2019/0380743, the full disclosure of which is incorporated herein by reference, is placed through the umbilicus U in the patient's abdomen A. As shown in FIG. 11C, the tool 200 is introduced into the distended abdomen to the level when semi-circular mid-portion segment 208 reaches the port seal S. As shown in FIG. 11D, the user after engaging the clutch, brings the robot arm 282 to the proximity of the tool side mount 240, depresses the mount lever 290 on the robot arm 282, engages the tool side mount 240 and by releasing the mount lever 290 locks the tool 200 to the robotic arm. Holding the clutch engaged and not displacing the position of semi-circular mid-portion segment 208 within the seal S, the user moves the robot arm 282 to align the robotic interphase 242 with the drive head 286 and locks it.

After the tool holder 282 is attached to the laparoscopic tool 200, the user, actuates the clutch to disengage the tool holder 282 and aligns the center point CP of the semicircular mid-portion 208 with a virtual insertion point prior to beginning the surgery, as shown in FIG. 11D. Typically, although not necessarily, the user will employ an alignment tool, such as alignment tools 260 and 266 previously described with reference to FIGS. 7 and 8. Once tool 200 and holder 282 are in alignment with the virtual insertion point, as shown by alignment line AL in FIG. 11D, the user can release the clutch release level, locking the tool and holder so that their motion will now be controlled by the robotic system (not manually). The laparoscopic tool 200 is then ready for use, although the surgery will often require that one, two, three, or even more laparoscopic tools be introduced through the seal, depending on the requirements of the surgery to be performed.

Figure 11E:
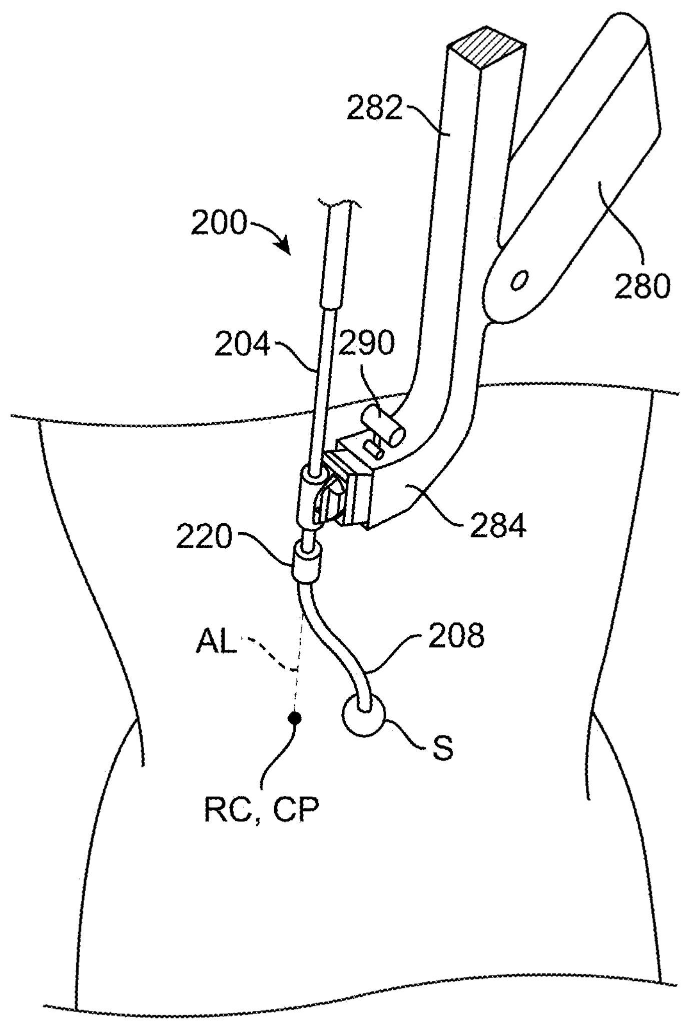

At any time during a surgical procedure, the user may desire to reposition the center point CP of the semi-circular mid-portion 208 with a different target virtual insertion point, as shown for example in FIG. 11E. The user can perform such repositioning by simply decoupling the arm 280 and the tool holder 282 from the surgical robot using the clutch release which is part of the surgical robot (not shown). The tool 200 and holder 282 can then be manually repositioned until the center point CP of the tool 200 is located at a different virtual insertion point, as shown in FIG. 11E. Such repositioning is accomplished without removing the tool 200 from the port seal S and without the need to form a penetration through the patient's abdomen at the new target virtual insertion point. While such repositioning is limited by the radius of the semi-circular mid-portion 208, a first tool can be exchanged for a second tool having a different semi-circular mid-portion radius, although tool removal will be necessary in that case.

During surgery, the robotic system will reposition the robot arm and tool at many different angles in relation to the plane of penetration of the abdominal wall with the pivot at the level of abdominal wall (remote center). Once the set-up is complete, the distance from a proximal portion of the laparoscopic tool held by the robotic arm to the virtual insertion point of this tool will typically remain the same. The initial distance is selected so a semi-circle center point and sharing the space remote center of the robotic arm 208 (FIGS. 7 and 8) is at the level of the virtual insertion point into the body cavity. From this time on, all movement of the robotic arm will maintain this distance so that the remote center remains the same location at the virtual insertion point into the abdominal wall.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for performing surgery, the method comprising:
- positioning a semi-circular mid-portion of a hollow shaft of a laparoscopic tool through a percutaneous passage of a patient;
- aligning a center point of the semi-circular mid-portion with a virtual insertion point; and
- operating the laparoscopic tool to cause an end effector to surgically interact with a tissue of the patient.

2. The method of claim 1, further comprising coupling the laparoscopic tool to a surgical robotic system.

3. The method of claim 2, wherein the surgical robotic system comprises at least one robotic arm and a tool holder, wherein the at least one robotic arm comprises a remote center.

4. The method of claim 3, wherein coupling the laparoscopic tool to the surgical robotic system comprises coupling a proximal section of the hollow shaft to the at least one robotic arm.

5. The method of claim 4, wherein coupling the proximal section of the hollow shaft to the at least one robotic arm comprises coupling the proximal section of the hollow shaft to a fixed tool side mount of the at least one robotic arm.

6. The method of claim 1, wherein aligning the center point of the semi-circular mid-portion with a virtual insertion point comprises using an alignment tool.

7. The method of claim 3, further comprising mounting the laparoscopic tool on the tool holder, wherein the center point coincides with the remote center.

8. The method of claim 7, wherein the percutaneous passage is offset from the remote center of the surgical robotic system by a distance equal to a radius of the semi-circular mid-portion.

9. The method of claim 3, further comprising disengaging the at least one robotic arm from the surgical robotic system to allow manual positioning of the at least one robotic arm.

10. The method of claim 9, further comprising manually positioning the at least one robotic arm to locate the center point of the semi-circular mid-portion of the hollow shaft at the virtual insertion point, wherein the semi-circular mid-portion is configured to remain positioned through the percutaneous passage.

11. The method of claim 10, wherein manually positioning the at least one robotic arm comprises rotating the semi-circular mid-portion of the hollow shaft around a common axis relative to a proximal section of the hollow shaft.

12. The method of claim 10, wherein manually positioning the at least one robotic arm comprises providing a visual marker of the location of the center point.

13. The method of claim 1, further comprising passing a flexible cable assembly through a central passage of the shaft of the laparoscopic tool.

14. The method of claim 3, further comprising:
- decoupling the at least one robotic arm and the tool holder from the surgical robotic system; and
- positioning the laparoscopic tool and the tool holder such that a center point of the laparoscopic tool is located at a second virtual insertion point.

15. The method of claim 1, further comprising:
- positioning a semi-circular mid-portion of a hollow shaft of a second laparoscopic tool through the percutaneous passage of the patient;
- coupling the second laparoscopic tool to a surgical robotic system;

aligning a center point of the semi-circular mid-portion of a hollow shaft of a second laparoscopic tool with a virtual insertion point; and operating the second laparoscopic tool to cause a second end effector to surgically interact with tissue.

16. The method of claim 15, further comprising interchangeably engaging the laparoscopic tool and the second laparoscopic tool.

17. The method of claim 15, further comprising coupling the second laparoscopic tool to the surgical robotic system.

18. The method of claim 15, further comprising passing a flexible cable assembly through a central passage of the hollow shaft of at least one of the laparoscopic tool or the second laparoscopic tool.

19. The method of claim 18, further comprising manipulating the flexible cable assembly using a driver.

20. The method of claim 1, further comprising providing a visual marker of a location of the center point.

21. The method of claim 1, wherein operating the laparoscopic tool comprises operating the laparoscopic tool while the mid-portion of the hollow shaft remains positioned in the percutaneous passage and the center point remains located at the virtual insertion point.

* * * * *